United States Patent [19]

Howard

[11] 4,041,153

[45] Aug. 9, 1977

[54] METHODS AND PHARMACEUTICAL PREPARATION FOR THE TREATMENT OF HYPERCHOLESTEROLAEMIA

[75] Inventor: Alan N. Howard, Cambridge, England

[73] Assignee: Bristol-Myers Company, New York, N.Y.

[21] Appl. No.: 583,308

[22] Filed: June 2, 1975

[30] Foreign Application Priority Data

June 4, 1974 United Kingdom ............... 24794/74

[51] Int. Cl.$^2$ ................... A61K 33/24; A61K 31/215; A61K 31/19

[52] U.S. Cl. .................................. 424/131; 424/308; 424/317

[58] Field of Search ............... 424/145, 153, 154, 131, 424/317, 308

[56] References Cited

PUBLICATIONS

Fleischman et al., Chem. Abst., vol. 66, (1967), p. 92861v.

Schroeder, Chem. Abst., vol. 68, (1968), p. 103061d.

The Merck Index, eighth ed., 1968, p. 270.

Primary Examiner—Sam Rosen
Attorney, Agent, or Firm—David M. Morse

[57] ABSTRACT

A composition for treatment of hypercholesterolemia contains clofibrate or a clofibrate derivative, a metal ion contributing compound which forms substantially insoluble metal bile acid salts and, optionally, a basic anion exchange resin. The composition components combine to give synergistic effect.

10 Claims, No Drawings

METHODS AND PHARMACEUTICAL PREPARATION FOR THE TREATMENT OF HYPERCHOLESTEROLAEMIA

The present invention relates to methods and pharmaceutical preparations for the treatment of hypercholesterolaemia.

It has long been recognized that certain conditions or diseases, such as coronary heart disease and atherosclerosis, are associated with and may be caused by the presence of too high a level of cholesterol in the blood plasma; and for the treatment of such condition many attempts have been made to find means for reducing the cholesterol level in blood plasma, for instance by provision of some kind of orally-administerable pharmaceutical preparation capable of exerting a hypocholesterolaemic effect, that is to say reducing the cholesterol level in blood plasma and thus combating hypercholesterolaemia.

It has now been found that, from amongst the wide variety of preparations, both in the nature of drugs and other products, which have hitherto been employed for the reduction of blood-cholesterol levels, it is possible to select combinations which exhibit a quite unexpectedly enhanced or synergistic effect, as will be described hereinafter. The selected combinations which display this peculiar and valuable therapeutic property are formed between certain known synthetic blood cholesterol-reducing drugs and certain metallic compounds. Although it is known that some of the latter can also reduce blood cholesterol, what is surprising is that when used in combination they can quickly achieve, in at least a large proportion of patients suffering from hypercholesterolaemia, a reduction in blood cholesterol which is greater than can be hoped for with one of the synthetic blood cholesterol-reducing drugs alone and also faster than could be expected with one of the metallic compounds alone, or even both of them jointly. The use of this synergistic combination of blood cholesterol-reducing agents thus opens the way to significant improvements in the treatment of hypercholesterolaemia.

The combination needed to attain these remarkable results is formed by the administration per os in a certain ratio (if appropriate separately but for convenience preferably in admixture) of both a. a hypocholesterolaemic compound of the general formula

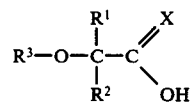

in which $R^1$ and $R^2$, which may be the same or different, are each a hydrogen atom or a substituted or unsubstituted alkyl, alkoxy, or phenoxy group, $R^3$ is a substituted or unsubstituted phenyl group and X is hydrogen (2 H) or oxygen, or an ingestible, non-toxic functional derivative of such compound, and b. an ingestible non-toxic metallic compound, capable of dissolution in the gastro-intestinal juices to yield a metallic salt or ion that can react with bile acids to form an insoluble or poorly soluble metal salt of these bile acids.

According to one aspect of the invention there is therefore provided a method for the treatment of hypercholesterolaemia, in which there is administered to the patient, per os:

a. one or more hypocholesterolaemic compounds of the general formula I and derivatives thereof defined before, and b. one or more ingestible non-toxic metallic compounds soluble in human gastro-intestinal juices to yield metal salts or ions which can react with bile acids to form insoluble or poorly soluble metal salts of these bile acids, the total amount of non-toxic metal being from 3.2 to about 90 eqivalents per mole of acid or alcohol of formula I and/or derivatives thereof.

It should be noted firstly that the ingestible nontoxic functonal derivatives of the hypocholesterolaemic compounds I include salts, esters and N-substituted or unsubstituted amides of the acids I and acyl derivatives of the alcohols I.

In calculating the ratio of metal to acid or alcohol, the equivalent weights of the metals are to be taken as the equivalents of the metals in the valency states in which they react with the bile acids and one mole of a di- or trivalent metal salt of the acid I is to be counted as two or three moles of the acid.

As previously indicated, although not absolutely necessary it is highly convenient to administer both the synthetic blood cholesterol-reducing drug(s) and also the metallic compound(s) simultaneously in the form of a simple admixture or formulated into some other, more sophisticated, pharmaceutical preparation and this invention will in the main be hereinafter described in terms of such preparations.

Thus, in another and more important aspect, this invention provides pharmaceutical formulations, for use in the treatment per os of hypercholesterolaemia, which comprise:

a. one or more compounds of the general formula (I) and/or ingestible non-toxic functional derivatives thereof; and b. one or more ingestible non-toxic metallic compound(s) soluble in human gastro-intestinal juices to yield metal salts or ions capable of reaction with bile acids to form insoluble or poorly soluble metal salts of these bile acids, the total amount of non-toxic metal being from 3.2 to 90 equivalents per mole of acid or alcohol I and/or derivative thereof, either alone or in combination with a pharmaceutical vehicle.

The class of blood cholesterol-reducing drugs which usually will be most preferred are the substituted carboxylic acids and derivatives thereof, which conform in free acids form to the general formula II:

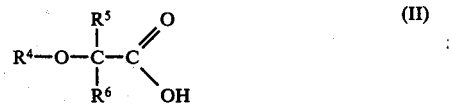

wherein $R^4$ is mono-, di- or tri-substituted phenyl group, bearing one, two or three identical or different substituents which are one or more of the following, namely halogen atoms and alkyl, alkoxy or hydroxy groups, and wherein $R^5$ and $R^6$ are each, independently, a hydrogen atom or an alkyl group.

The preferred blood cholesterol-reducing drug(s) of general formula II above for use in this invention are those in which the aromatic group $R^4$ is a monosubstituted phenyl group, in particular the p-chlorophenyl, p-ethoxyphenyl or o-chlorophenyl group, and/or in which the groups $R^5$ and $R^6$ are alkyl groups containing not more than 6 carbon atoms, and above all when they are both methyl groups.

Although for convenience the blood cholesterol-reducing drugs(s) of general formula I above have been shown in free acid or free alcohol form, it is frequently preferred to employ them in the form of suitable derivatives, such as esters and salts of the acid or acyl derivatives of the alcohol. The preferred esters are the methyl, ethyl, n-propyl and n-butyl esters, and the preferred salts are the sodium, potassium, calcium, magnesium, aluminium, zinc bismuth and iron salts; the preferred acyl derivatives are derived from lower aliphatic acids, such as acetic acid, propionic acid or butyric acid.

Experience so far indicated that the most preferred of the synthetic organic blood cholesterol-reducing drugs of general formula II for use in accordance with this invention are p-chlorophenoxy-iso-butyric acid and its derivatives, especially its ethyl ester (known as "Clofibrate"), and its salts. The most exhaustive tests have been undertaken with these blood cholesterol-reducing drug(s), and their excellent activity in accordance with this invention recommends their use, as will be apparent hereinafter.

The following compounds of general formula II are also recommended for use in accordance with this invention, namely the methyl-phenoxyisobutyric acids, the 2- and 3-chlorophenoxyisobutyric acids; 2,4-dichloro- and 2,4,5-trichlorophenoxyisobutyric acids; the methoxyphenoxyisobutyric acids; the methyl-chlorophenoxyisobutyric acids such as 3-methyl-4-chlorophenoxyisobutyric acid; α-(para-chlorophenoxy)-propionic acid; and α-(para-chlorophenoxy)-n-butyric acid, as well as the methyl, ethyl, n-propyl and n-butyl esters thereof, the sodium, potassium calcium, magnesium, zinc, iron, bismuth and aluminium salts thereof, and the amides thereof, optionally N-substituted by lower alkyl (1–4 C), particularly ethyl.

As regards the ingestible non-toxic metal compounds for use in this invention it is preferred to use a calcium, magnesium, aluminium or bismuth compound, calcium compounds being especially preferred inter alia for reasons of economy. In general, one may employ any ingestible oxide, hydroxide or non-toxic salt of these or other suitable metals which is capable of dissolution in the gastro-intestinal juices of the patient, so as there to yield a corresponding salt or iron capable of reaction with bile acids to form insoluble salts which can be excreted in the faeces. The choice of such metal compounds is of course wholly within the competence of anyone with knowledge concerning pharmaceutical formulations, and can therefore be left to them. Suitable calcium compounds for use in this invention include calcium hydroxide as well as calcium carbonate, bicarbonate, chloride, gluconate, glucono-galacto-gluconate, lactate, acetate, citrate, mono- and di- and tri-phosphate, levulinate, saccharate and glycerophosphate. The preferred calcium compounds usually are calcium carbonate and/or calcium chloride. Suitable aluminium compounds are the oxide, hydroxide, chloride, phosphate, sulphate, silicate, stearate and carbonate, whilst suitable magnesium compounds are the oxide, hydroxide, aluminate, carbonate, silicate, chloride, citrate, phosphate, lactate, stearate and sulphate. Finally, suitable bismuth compounds are the oxide, aluminate, subnitrate, carbonate, oxychloride and tartrate.

The metallic compounds may be administered in any convenient form, either solid or (where possible) liquid, but will normally be used most readily in the form of fine particles or powder, sieved to eliminate any oversize material, and where appropriate then agglomerated — when desired, after admixture with the cholesterol-reducing drugs — and filled into capsules or compressed into tablets.

It is however essential, if the desired results are to be attained, for the ratio of the metallic compounds used in accordance with this invention to be kept within the range, relative to the blood cholesterol-reducing drug(s) of general formula I, of from 3.2 to 90 equivalents of metal per mole. Thus the proportion of calcium or other metal exceeds the stoichiometric amount in which the calcium or other metal combines with the blood cholesterol-reducing drug(s) I — if in free acid form — to build the corresponding calcium or other metal salt of the drug(s). The use of such calcium or other metal salts of the blood cholesterol-reducing drug(s) is within the scope of this invention but only so long as sufficient additional calcium or other metal compound(s) is present to bring the ratio up to at least 3.2 equivalents per mole; the use of the calcium or other metal salt alone without such an excess-forming addition, dos not make it possible to attain the desired enhanced results.

The upper limit of about 90 equivalents of metal per mole is quite a practical limit. In fact, the upper level is determined by the daily dosage of metal which can be administered to the patient without inducing severe side-effects. This maximal daily dosage is varying from metal to metal. For guidance a daily doage of 5 g of calcium, 10 g of aluminium, 5 g of magnesium or 10 g of bismuth is held to be the upper level that may be administered. For other metals this upper level varies within the same range of 5 to 10 g per day.

In fact, not merely a small excess of metal but a relatively large one is neded if one is to secure optimum results. As will be demonstrated hereinafter, the admixture of the blood cholesterol-reducing drug(s) of general formula I with the metallic compounds has a synergistic effect in the reduction of cholesterol values in human plasma, which is useful over the entire molar range of proportions of from 3.2 to 90 eqivalents per mole but to obtain the maximum from the invention it is preferred to use mixtures in the proportions of from 4 to 40 equivalents per mole and and more especially of from 4 to 20 equivalents per mole. In fact, the most preferred ratio is substantially 4 to 15 equivalents per mole.

In the case of the especially preferred compositions in which the compound of general formula I is Clofibrate and the metal is calcium, this means that synergistic effects are observed over a Clofibrate: calcium weight ratio in the range of from 1:7.5 to 4:1. The preferred Clofibrate: calcium weight ratios are in the range of from 1:3 to 3:1 and the especially preferred ratios are in the range of 1:1.6 to 3:1. The most preferred ratio using calcium is about 2:1.

As will be obvious, for special purposes flavouring materials (such as orange oil) and synthetic sweeteners (such as saccharine and saccharine sodium) may be added to the individual drug(s) and/or metallic compound(s) as can also edible colouring matters and/or carriers and/or faecal softeners and/or surfactants.

For certain purposes it may be useful to add certain other drugs to potentiate the hypocholesterolaemic action of the combination. Lipolytic compounds such as poly-unsaturated phosphatidyl choline obtained from soya are particularly beneficial in this respect.

A particularly excellent hypocholesterolaemic effect is achieved if in addition to a metallic salt and compounds of formula I, an anion exchange resin is employed in the compositions for use in this invention. Preferably, the total amount of anion exchange resin employed in the compositions is from 50 to 8000g per mole and most preferably from 150 to 3000g per mole, of the compound of formula I.

Any type of basic non-toxic anion exchange resin may be used in the compositions of the present invention. The resin can be, for example, a water-insoluble synthetic polymer or a polysaccharide substituted with amino groups (which may be quaternised). The products may be cross-linked or non-cross-linked.

One particularly preferred type of resin is the ω-dialkylaminoalkyl, ω-aminoalkyl, ω-guanidinoalkyl and the ω-(para-aminophenyl)alkyl ethers of polysaccharides (which may be cross-linked or non-cross-linked) and their derivatives, and the non-toxic salts formed by such ethers with acids. The preferred polysaccharide bases of these resins are dextran cross-linked with epichlorohydrin or cellulose, and the preferred ethers are those in which the or each alkyl group contains from 1 to 4 carbon atoms. The preferred dextrans are the anhydroglucose polymers produced by the action of various strains of Leuconostoc upon aqueous solutions of sucrose, and the water-insoluble cross-linked dextrans produced by the action of bifunctional compounds upon water-soluble dextrans (such as the resins described in U.S. Pat. No. 3,042,667). Cross-linked water-insoluble celluloses are produced by the same methods. Desirably, the amino-alkyl groups in the resins are the 2-diethylaminoethyl, aminoethyl, guanidinoethyl and p-aminobenzyl groups. Such compounds are for example described in U.S. Pat. No. 3,227,025. The preferred salts of these compounds are the hydrochlorides.

Another preferred type of basic non-toxic anion exchange resin which may be used in the compositions of the invention is the water-insoluble high molecular weight reaction products obtained by reaction of a polyalkylene polyamine with epichlorohydrin and/or glycerol-1,3-dichlorohydrin and/or an aliphatic bis-epoxy compound (such as 1,2:3,4-bis-epoxybutane, bis-epoxypropyl ether or a bis-epoxypropyl ether of an α,ω-alkylene glycol. The preferred polyalkylene polyamines for use in the reaction are the polyethylene polyamines such as triethylenetetramine, tetraethylenepentamine and pentaethylenehexamine: such compounds contain at least as many secondary amino groups as primary amino groups in the molecule. Desirably, in the reaction products a proportion of the amino grouos are quaternised and form chloride salts; this is conveniently done by bringing the co-polymer to pH4 with HCl and drying it.

A third preferred type of basic non-toxic anion exchange resin which may be used in the compositions of the invention is those resins formed by polymerisation of an ethylenically-unsaturated monmer containing at least one amino group, the amino groups in the resin being quaternised. Such resins may be prepared either by polymerising a pre-quaternised monomer or by first polymerising an unquaternised monomer and then quaternising the resultant product. The ethylenically-unsaturated monomer is desirably a compound of the general formula:

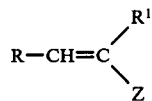

(in which R is hydrogen atom or a methyl, phenyl, carboxy, carboxymethyl or carboxyethyl group;

$R^1$ is a hydrogen atom, a methyl group or a group of the formula —$CH_2$ COOX in which X is a hydrogen atom or an alkyl group having one to four carbon atoms; and Z is a pyridinium or carboxylic ester grouping which is free from aliphatic unsaturation and Which contains a quaternary ammonium group, for example a carboxyalkyl group terminated by a quaternary alkyl-ammonium group). Preferred monomers are vinyl-pyridine, α-methylvinylpyridine and the acrylic, methacrylic, crotonic, cinnamic and α-methylcinnamic esters of the ω-dialkylaminoalkanols in which each of the N-alkyl groups contains not more than four carbon atoms. The quaternization of the amino groups before or after polymerisation may be effected by reaction with an alkyl halide, a dialkyl sulphate or a trialkyl phosphate. In order to secure adequate spacing of the quaternary groups this third group of anion exchange resins conveniently incorporate one or more ethylenically-unsaturated monomers which are free from amino groups, that is they are conveniently copolymers between an amino-bearing monomer and a monomer which does not contain amino-groups. Depending upon the nature of the non-amino comonomer or comonomers used these resins may be of an essentially linear structure or may be cross-linked. When a linear copolymer is to be produced the copolymerizing monomer should be a monoethylenic monomer free from groups which could interfere with the basic action of the quaternary amino groups in the final polymer, that is free from ionizable groups and hydrophobic groups. Examples of suitable non-amino monomers for use in this class of resins are alkyl methacrylates in which the alkyl group contains one to four carbon atoms (such as methyl methacrylate), monocyclic aromatic hydrocarbons and halohydrocarbons containing a vinylidene group such as styrene, α-methylstyrene and ω-chlorostyrene, vinyl alkanoates having one to four carbon atoms in the alkanoate group (such as vinyl acetate) and ethylenically-unsaturated nitriles (such as acrylonitrile and methacrylonnitrile). Such nonamino monomers are preferably used in an amount not exceeding 50% of the weight of the amino-containing monomer.

Alternatively or additionally, the resin may be one made by polymerising the amino-containing monoethylenically unsaturated monomer with not more than 20% (based upon the total weight of all the co-monomers), of a monomer which is free from ionizable groups and contains at least two ethylenically-unsaturated groups. Examples of such monomers are methylene bis-acrylamide and bis-methacrylamide, alkylene glycol bis-acrylates and alkylene bis-methacrylates (such as ethylene bis (methacrylate)), the divinyl monocyclic aromatic hydrocarbons (such as divinylbenzene), the tris(alkenylamines (such as triallylamine) and polyalkenylated polyols or sugars (such as triallylpentaerythritol and polyallyl sucrose). Whether or not either type of comonomer is employed, the polymerisation is conveniently effected in an aqueous or alcoholic medium in the presence of a catalyst (such as a permonosulphate, perbenzoic acid or an azo compound such as azobis(isobutyronitrile) which acts as a source of free radicals.

A fourth preferred type of basic non-toxic anion exchange resin for use in the compositions of the present invention is a styrene polymer substituted with basic groups. Such a resin may be made by copolymerizing styrene with a minor proportion (preferably not more than 5% by weight) of divinylbenzene. The resulting copolymer is then chloromethylated and the product treated with a tertiary amine, preferably a trialkylamine containing not more than 10 carbon atoms, so as to introduce quaternary ammonium groups. The extent of chloromethylation and hence the proportion of quaternary groups can be varied over quite wide limits.

Amongst the above mentioned resins, it has been found that particularly good results have been obtained with the diethylaminoethyl celluloses and dextrans, especially with the product (Secholex (PDX chloride or poly-[2-(diethylamino)ethyl]-polyglycerylene dextran hydrochloride), cholestyramine (which is a cross-linked styrene polymer containing tertiary amino groups) and colestipol (which is a polyethylene polyamine-epichlorohydrin condensation product) are also very effective.

The treatment in accordance with this invention may be carried out along conventional lines, in the sense that the daily doses of the cholesterol-reducing drug(s) of general formula I and the metallic compound which are administered, either separately or in conjunction with one another, should in accordance with this invention be more or less the same as the respective amounts in which they have individually been administered in accordance with conventional therapeutic practice.

Thus for instance, when the blood cholesterol-reducing drug of general formula I employed is ethyl para-chlorophenoxyisobutyrate (clofibrate) the normal conventional dose is 1.5 – 2.5 g/day, and the dose cannot be increased above this 2.5 g/day upper limit without danger of gastrointestinal side effects. Similarly, the normal conventional dose of calcium to obtain a therapeutic response is 0.8 – 2.0 g/day, and above that 2.0 g/day upper level of intake the danger of deposition of calcium in organs such as the kidney is increased as is the risk of unpleasant side-effects such as constipation. When an anion exchange resin is also employed the normal conventional dose of such a resin is 3–40 g/day.

It is desirable when practising the present invention is adhere to the same upper limits, in order to avoid the same dangers - but whereas these dangers preclude one from obtaining a better response to each individual treatment by simply increasing the respective dosage, the use of a combination of ethyl p-chlorophenoxyisobutyrate and a calcium salt in conjunction with one another enables one to obtain a lower blood cholesterol level, because of the synergism exhibited, and thus an increased therapeutic effect, without increasing the side-effects; and moreover, since calcium salts are very inexpensive compared with ethyl p-chlorophenoxyisobutyrate, one could more cheaply achieve the same level of response with a mixture of calcium and ethyl p-chlorophenoxyisobutyrate than with the latter alone, while one could with the mixture achieve a greater and much speedier response than with the calcium alone.

In order further to demonstrate the remarkable therapeutic results attainable in accordance with this invention, the results of certain clinical trials will be reported below. At this point it should be noted that a certain number of the patients tested, but only quite a small percentage, appeared to be resistant to the blood cholesterol-reducing effect of one or other of the blood cholesterol-reducing agents employed (which is common clinical experience in the case of blood cholesterol-reducing agents) and with such patients naturally no significant effect could be observed. To maintain accuracy, the results obtained with such patients have therefore been eliminated from the clinical test results reported below:

CLINICAL TEST RESULTS

Procedure

Patients were asked to continue on their normal diet, and blood was taken after an overnight fast. After four weeks without treatment they were given Clofibrate Atromid-S, 0.5 g three times daily), calcium carbonate (0.65 g three timed daily) or a combination of both. After each four weeks treatment there was a period of four weeks without treatment before the next treatment was started. Serum choleterol was determined by the auto-analyser and triglycerides by the method of Thorp and Stone.

Results

It will be seen that on treatment with Clofibrate a mean reduction of 11% in the serum cholesterol was obtained (Table 1). One patient showed no response. With calcium carbonate only a 4% decrease was seen. When both Clofibrate and calcium carbonate were used in combination a 23% reduction was observed. Thus, the average reduction was over 50% greater than the sum of the individual effects on the same patients.

Clofibrate caused a mean 35% decrease in serum triglycerides when given alone. Calcium carbonate had no influence on serum triglycerides given alone or in combination (Table 2).

TABLE 1

EFFECT OF CLOFIBRATE (A) AND CaCO$_3$ (X) ALONE AND IN COMBINATION ON SERUM CHOLESTEROL (mg/100 ml)

| Patient | Nil | After A | % change (decrease) | Nil | After X | % change (decrease) | Nil | After A + X | % change (decrease) |
|---------|-----|---------|---------------------|-----|---------|---------------------|-----|-------------|---------------------|
| P | 265 | 215 | 19 | 270 | 260 | 4 | 265 | 190 | 28 |
| R | 290 | 250 | 14 | 295 | 280 | 5 | 290 | 225 | 22 |
| F | 310 | 300 | 3 | 305 | 295 | 4 | 300 | 260 | 13 |
| B | 255 | 230 | 10 | 260 | 255 | 2 | 250 | 180 | 28 |
| H | 255 | 235 | 8 | 250 | 240 | 4 | 255 | 195 | 24 |
|   |     |     | 11 |     |     | 4  |     |     | 23 |

TABLE 2
EFFECT OF CLOFIBRATE (A) AND CaCO₃ (X) ALONE AND IN COMBINATION ON SERUM TRIGLYCERIDES
(mg/100 ml)

| Patient | Nil | A | % change | Nil | X | % change | Nil | A + X | % change |
|---|---|---|---|---|---|---|---|---|---|
| P | 220 | 140 | 36 | 235 | 240 | 6 | 240 | 125 | 48 |
| R | 190 | 140 | 26 | 195 | 185 | 5 | 195 | 135 | 31 |
| F | 870 | 386 | 56 | 670 | 680 | 0 | 750 | 456 | 39 |
| B | 70 | 70 | 0 | 75 | 80 | +6 | 75 | 75 | 0 |
| H | 160 | 67 | 58 | 140 | 135 | 4 | 155 | 67 | 57 |
|   |   |   | 35 |   |   | 2 |   |   | 35 |

EFFECT OF CLOFIBRATE AND METALLIC IONS ON SERUM CHOLESTEROL IN PATIENTS

Procedure

Patients were selected with a serum cholesterol of greater than 235 mg/100 ml. Following three baseline determinations they were randomly allocated to the following treatments:

a. Clofibrate (Atromid-S) 1.5 g/day,
b. Clofibrate 1.5 g/day + calcium carbonate 2g/day,
c. Clofibrate 1.5 g/day + aluminium hydroxide 2.4 g/day,
d. Clofibrate 1.5 g/day + magnesium hydroxide 2.4 g/day,
e. Clofibrate 1.5 g/day + magnesium hydroxide 2.4 g/day + aluminum hydroxide 2.4 g/day,
f. Calcium carbonate 2 g/day,
g. Magnesium hydroxide 2.4 g/day,
h. Aluminium hydroxide 2.4 g/day,
i. Clofibrate 1.5 g/day + bismuth hydroxide 2.0 g/day.

Treatment was for 4 weeks in each case, followed by 4 weeks placebo, before continuing with a different treatment. Divided doses were given thrice daily. Serum cholesterol was analysed by the autoanalyser using the Zak reaction.

Results

A comparison of values obtained are shown in Table 3.

Comments

It will be seen that a combination of compounds containing the metallic ions, calcium, aluminium and magnesium, with clofibrate, gave a greater decrease in serum cholesterol then the sum of the decreases achieved by each compound given separately.

A much greater decrease in serum cholesterol was seen in one patient treated with bismuth and clofibrate, than with clofibrate alone.

TABLE 3
Serum cholesterol (mg/100 at) in patients treated with clofibrate and supplements

| Patient No. | Clofibrate 1 | 2 | Δ | Calcium 1 | 2 | Δ | Clofibrate + Calcium 1 | 2 | Δ | Clofibrate + Aluminium 1 | 2 | Δ |
|---|---|---|---|---|---|---|---|---|---|---|---|---|
| 1 | 280 | 225 | −55 | 293 | 290 | −3 | 275 | 195 | −80 | 280 | 190 | −90 |
| 2 | 258 | 240 | −18 | 245 | 263 | +18 | 263 | 212 | −51 | 245 | 215 | −30 |
| 3 | 310 | 278 | −32 |   |   |   | 305 | 265 | −40 | 310 | 250 | −60 |
| 4 | 305 | 230 | −75 |   |   |   |   |   |   |   |   |   |
| 5 | 253 | 210 | −43 |   |   |   | 255 | 205 | −50 | 245 | 185 | −60 |
| 6 | 240 | 200 | −40 |   |   |   |   |   |   | 253 | 190 | −63 |
| 7 | 250 | 197 | −53 | 258 | 256 | −2 | 250 | 187 | −63 |   |   |   |
| 8 | 237 | 207 | −30 | 230 | 223 | −7 | 230 | 187 | −47 |   |   |   |
| 9 | 250 | 205 | −45 |   |   |   |   |   |   | 250 | 190 | −60 |
| 10 | 250 | 243 | −7 | 250 | 240 | −10 | 253 | 183 | −70 | 245 | 200 | −45 |
| 11 | 250 | 240 | −10 | 235 | 255 | +20 | 245 | 182 | −63 |   |   |   |
| 12 | 260 | 223 | −37 | 255 | 245 | +10 | 267 | 215 | −52 |   |   |   |
| 13 | 245 | 207 | −38 |   |   |   |   |   |   |   |   |   |
| 14 | 290 | 235 | −55 |   |   |   | 287 | 210 | −77 | 290 | 205 | −85 |
| 15 | 250 | 215 | −35 | 247 | 257 | +10 | 250 | 195 | −65 |   |   |   |
| 16 | 305 | 290 | −15 | 305 | 305 | 0 |   |   |   | 310 | 258 | −52 |
| 17 | 265 | 227 | −48 |   |   |   | 270 | 220 | −50 |   |   |   |

| Patient No. | Clofibrate − Magnesium 1 | 2 | Δ | Clofibrate + Bismuth 1 | 2 | Δ | Clofibrate + Aluminium + Magnesium 1 | 2 | Δ | Magnesium 1 | 2 | Δ | Aluminium 1 | 2 | Δ |
|---|---|---|---|---|---|---|---|---|---|---|---|---|---|---|---|
| 1 |   |   |   |   |   |   |   |   |   |   |   |   | 290 | 295 | +5 |
| 2 | 248 | 205 | −43 |   |   |   |   |   |   | 253 | 260 | +7 | 260 | 253 | −7 |
| 3 | 305 | 268 | −37 | 305 | 233 | −72 | 310 | 265 | −45 |   |   |   |   |   |   |
| 4 | 320 | 220 | −100 |   |   |   | 325 | 215 | −110 |   |   |   |   |   |   |
| 5 | 255 | 205 | −50 |   |   |   | 255 | 185 | −60 |   |   |   | 263 | 265 | +2 |
| 6 | 245 | 200 | −45 |   |   |   | 240 | 180 | −60 |   |   |   | 270 | 267 | −3 |
| 7 |   |   |   |   |   |   |   |   |   |   |   |   |   |   |   |
| 8 |   |   |   |   |   |   |   |   |   |   |   |   |   |   |   |
| 9 |   |   |   |   |   |   | 240 | 185 | −55 |   |   |   |   |   |   |
| 10 | 245 | 203 | −42 |   |   |   | 243 | 185 | −58 | 255 | 260 | +5 |   |   |   |
| 11 | 245 | 220 | −25 |   |   |   |   |   |   |   |   |   |   |   |   |
| 12 |   |   |   |   |   |   | 245 | 190 | −55 |   |   |   |   |   |   |
| 13 | 245 | 183 | −62 |   |   |   |   |   |   | 250 | 240 | −10 |   |   |   |
| 14 | 285 | 187 | −98 |   |   |   |   |   |   |   |   |   | 298 | 305 | +7 |
| 15 | 250 | 210 | −40 |   |   |   |   |   |   |   |   |   |   |   |   |
| 16 | 305 | 270 | −35 |   |   |   | 300 | 258 | −42 | 295 | 300 | +5 |   |   |   |
| 17 | 265 | 213 | −52 |   |   |   | 270 | 215 | −55 |   |   |   |   |   |   |

1 = before treatment

EFFECT OF CLOFIBRATE AND CALCIUM AT DIFFERENT RATIOS

A number of patients with initial serum cholesterol levels of 250–300 mg/100 ml were treated for one month with preparations containing a variety of ratios of clofibrate and calcium. The preparations used are set out in Table 4 below. Between two treatments a one month placebo was administered to the patients.

Results

The results of the treatments, in terms of the decrease in serum cholesterol levels following treatment, are given in Table 4 below.

It may be seen that there was little or no potentiation of the effect of clofibrate by calcium where the ratio of calcium to clofibrate was less than 3.2 equiv/mole. At a ratio of 3.2 equiv/mole there was a significantly greater decrease in serum cholesterol than achieved with clofibrate above. As the ratio of calcium to clofibrate was increased, the decrease in serum cholesterol achieved by the treatments became even more marked. At 4.2 equiv/mole a particularly significantly greater lowering of the serum cholesterol may be observed.

Conclusions

The threshold at which the effect of calcium becomes apparent is in the region of 3.2 equiv/mole, while an optimum calcium to clofibrate ratio would appear to lie in the region of 4 equiv/mole. Above this level there is a smaller enhancement of the hypocholesterolaemic effect and higher ratios are not therefore recommended particularly as there may be an increased incidence of renal stones with very high levels of calcium.

TABLE 4

| Calcium Carbonate (g/day) | Clofibrate (g/day) | Ratio Ca/clofibrate (equiv/mole) | 1 | 2 | 3 | 4 | 5 | 6 | 7 | 8 | 9 | Mean decrease (mg/100 ml) |
|---|---|---|---|---|---|---|---|---|---|---|---|---|
| 0 | 1.5 | 0 | 37 | 35 | 50 | 25 | 15 | — | — | — | — | 32.4 |
| 0 | 1.5 | 0 | — | — | — | — | — | 55 | 18 | 40 | 7 | 30.0 |
| 0.33 | 1.5 | 1.0 | 35 | 38 | 55 | 23 | 10 | — | — | — | — | 32.2 |
| 0.65 | 1.5 | 2.1 | 40 | 39 | 68 | 25 | 12 | — | — | — | — | 36.8 |
| 1.0 | 1.5 | 3.2 | — | — | — | — | — | 65 | 25 | 40 | 30 | 40.0 |
| 1.30 | 1.5 | 4.2 | 60 | 85 | 120 | 93 | 87 | — | — | — | — | 89.0 |
| 1.95 | 1.5 | 6.3 | 65 | 95 | 130 | 90 | 85 | — | — | — | — | 93.0 |
| 2.0 | 1.5 | 6.5 | — | — | — | — | — | 80 | 51 | 43 | 70 | 61.0 |

EFFECT OF A COMBINATION OF PDX CHLORIDE, CLOFIBRATE AND METALLIC SALTS

Twelve patients with hypercholesterolaemia were treated with placebo for three months and then with a combination of PDX chloride (15g/day) and clofibrate (1.5g/day) for a further three months. The addition of metallic salts to the treatment was then made to eight of the twelve patients as shown in Table 5, whilst the remaining four patients received no additional treatment. Serum cholesterol estimations were carried out on the patients each month.

Results

As shown in Table 5, the addition of magnesium, calcium and aluminium salts gave a further significant decrease in serum cholesterol, whilst those patients without such supplementation remained unchanged.

TABLE 5

Effect of combinations of matallic cations, clofibrate and PDX chloride

| Patient No. | 1 S.Ch. | | 2 S.Ch. | | 3 S.Ch. | | 4 S.Ch. | | 5 S.Ch. | | 6 S.Ch. | |
|---|---|---|---|---|---|---|---|---|---|---|---|---|
| | PL | 320 | PL | 250 | PL | 245 | PL | 293 | PL | 385 | PL | 506 |
| | | 315 | | 273 | | 293 | | 255 | | 370 | | 520 |
| | | 300 | | 278 | | 263 | | 253 | | 368 | | 500 |
| | S+A | 255 | S+A | 180 | S+A | 193 | S+A | 197 | S+A | 300 | S+A | 360 |
| | | 240 | | 177 | | 183 | | 173 | | 285 | | 375 |
| | | 240 | | 183 | | 210 | | 180 | | 280 | | 350 |
| | +Mg | 220 | S+A+Mg | 158 | S+A+Mg | 197 | S+A+λMg | 168 | S+A+λMg | 290 | S+A+Ca | 290 |
| | | 243 | | 185 | | 205 | | 197 | | 295 | | 307 |
| | | 260 | | 168 | | 183 | | 165 | | | | 303 |
| | | 225 | | | | 215 | | 187 | S+A+Ca | 257 | | |
| | | 270 | S+A+Ca | 150 | | 195 | | 155 | | 257 | S+A+Mg | 343 |
| | | 215 | | 143 | | | | | | 273 | | 325 |
| | | | | | S+A+Ca | 187 | S+A+Ca | 153 | | | | 307 |
| | | | | | | 165 | | 135 | | | | 363 |
| | S+A+Ca | 200 | | | | 185 | | 145 | | | | 345 |
| | | 205 | | | | 183 | | 145 | | | | 345 |
| | | 203 | | | | | | 145 | | | | |
| | | | | | | | | | | | S+A+Mg Al | 335 |
| | | | | | | | | | | | | 287 |

| Patient No. | 7 S.Ch. | | 8 S.Ch. | | 9 S.Ch. | | 10 S.Ch. | | 11 S.Ch. | | 12 S.Ch. | |
|---|---|---|---|---|---|---|---|---|---|---|---|---|
| | PL | 500 | PL | 620 | PL | 430 | PL | 350 | PL | 300 | PL | 275 |
| | | 520 | | 520 | | 425 | | 375 | | 280 | | 270 |
| | | 500 | | 595 | | 450 | | 355 | | 295 | | 260 |
| | S+A | 387 | S+A | 325 | S+A | 320 | S+A | 300 | S+A | 205 | S+A | 195 |
| | | 367 | | 327 | | 315 | | 295 | | 195 | | 190 |
| | | 343 | | 330 | | 335 | | 295 | | 210 | | 180 |

TABLE 5-continued

| | | | | | | | | | | | | |
|---|---|---|---|---|---|---|---|---|---|---|---|---|
| \multicolumn{13}{c}{Effect of combinations of matallic cations, clofibrate and PDX chloride} |
| S+A+Ca | 287 | S+A+Al | 305 | S+A | 330 | S+A | 305 | S+A | 210 | S+A | 183 |
| | 307 | | 323 | | 325 | | 290 | | 205 | | 195 |
| | | | 297 | | 340 | | 300 | | 200 | | 198 |
| | | S+A+Mg | 297 | | | | | | | | |
| | | | 330 | | | | | | | | |
| | | | 340 | | | | | | | | |
| | | | 303 | | | | | | | | |
| | | S+A+Mg/Al | 300 | | | | | | | | |
| | | | 336 | | | | | | | | |
| | | S+A+Ca | 295 | | | | | | | | |
| | | | 307 | | | | | | | | |
| | | | 295 | | | | | | | | |
| | | | 303 | | | | | | | | |

In the above Table:
PL = placebo
S = Secholex (15g/day), PDX chloride
Mg = magnesium hydroxide (2.4g/day)
Ca = calcium carbonate (1.0 g/day)
Al = aluminum hydroxide (2.4 g/day)
Mg/Al = combination of magnesium and aluminium hydroxides (2.4 + 2.4g = 4.8g/day)
A = clofibrate (1.5g/day)
S.Ch. = serum cholesterol level (mg/100ml) for each treatment The following Examples illustrate the compositions of the present invention.

EXAMPLE 1

Mixture of powder and liquid.

| | | |
|---|---|---|
| Calcium carbonate powder | 100 | g |
| ethyl para-chlorophenoxyisobutyrate | 100 | g |
| Talc (U.S.P) | 10 | g |
| Magnesium stearate (U.S.P.) | 0.5 | g |

The finely powdered ingredients were thoroughly mixed and then filled into hard gelatin capsules for oral use, each capsule containing 500 mg. The capsules were taken thrice daily with meals.

In the above example, the para-chlorophenoxyisobutyric ester may be replaced by an equivalent amount of phenoxyisobutyric acid, 2-methyl, 3-methyl, or 4-methyl-phenoxyisobutyric acid, 3-chlorophenoxyisobutyric acid, 4-bromophenoxyisobutyric acid or 3-methyl-4-chlorophenoxyisobutyric acid or an ester thereof.

EXAMPLE 2

Mixture of a powder and micro-encapsulated liquid.

| | | |
|---|---|---|
| Calcium carbonate powder | 100 | g |
| ethyl para-chlorophenoxyisobutyrate (micro-encapsulated) | 150 | g |
| flavouring | 5 | g |
| gum arabic powder | 25 | g |

Because the ethyl ester has an unpleasant taste, it is conveniently mixed with the other components in the form of micro-capsules. The ethyl ester is micro-encapsulated to give a pore size of about 150 microns and then mixed with the other ingredients.

In this Example the ethyl para-chlorophenoxyisobutyrate may be replaced by an equal weight of n-propyl para-chlorophenoxyisobutyrate.

EXAMPLE 3

Mixture of powders.

| | | |
|---|---|---|
| sodium salt of para-chlorophenoxyisobutyric acid | 100 | g |
| calcium chloride | 100 | g |
| methyl cellulose | 10 | g |
| Talc | 10 | g |
| calcium stearate | 10 | g |

The sodium salt, calcium chloride are mixed well, granulated into three tablets (500 mg) for oral use and swallowed thrice daily with meals.

In the above Example, the sodium salt of para-chlorophenoxyisobutyric acid may be replaced by an equivalent amount of its potassium, calcium or aluminum salt.

EXAMPLE 4

Oil suspension.

| | | |
|---|---|---|
| parachlorophenoxyisobutyric acid | 100 | g |
| calcium carbonate | 100 | g |
| oil base | 1000 | ml |

The above ingredients are mixed together for oral use. The oil base consists of equal parts of soya bean oil and purified linseed oil gelled with 1% by weight of aluminium monostearate. One teaspoonful is administered three times a day with meals.

EXAMPLE 5

Mixture with a third component which potentiates activity.

| | | |
|---|---|---|
| polyunsaturated phosphatidyl choline (from soya beans) | 250 | g |
| ethyl parachlorophenoxyisobutyrate | 250 | g |
| calcium carbonate | 250 | g |
| α-tocopherol acetate | 2.5 | g |
| mono- and di-glycerides | 120 | g |
| soya bean oil | 140 | g |

The soya bean oil is mixed with the glyceride mixture and then polyunsaturated phosphatidyl choline is dissolved with stirring and if necessary with heating in a water bath at 40°–50° C while protected by an inert gas, preferably also with exclusion of light. The α-tocopherol and ethyl ester were then added and the calcium carbonate worked in to give an oil suspension. The whole is then filled into hard gelatin capsules each containing 500 mg. Three capsules are given thrice daily with meals.

In the above Example, the ethyl para-chlorophenoxyisobutyrate may be replaced by an equal weight of 4-methoxyphenoxyisobutyric acid, 2:4-dichlorophenoxyisobutyric acid or 2:4:5-trichlorophenoxyisobutyric acid.

EXAMPLE 6

An emulsion.

| | | |
|---|---|---|
| cane sugar | 200 | g |
| sodium benzoate | 1 | g |
| pyridoxine HCl | 0.6 | g |
| calcium carbonate | 750 | g |
| polyethylene sorbitanmono-oleate condensate | 10 | g |
| ethyl p-chlorophenoxyisobutyrate | 500 | g |
| soya bean lecithin | 25 | g |
| mixed tocopherol | 2.4 | g |
| propyl gallate concentrate | 0.05 | g |
| water | 400 | ml |

The cane sugar, sodium benzoate, pyridoxine, condensate, are dissolved in the water and stirred into a mixture of the ester, lecithin, tocopherols and gallate. The calcium carbonate is then added and the resulting emulsion suspension is homogenised by passing through a conventional homogeniser. There is thus obtained an emulsion suitable for oral administration for therapeutic purposes. About two teaspoonfuls (10 ml) are given three or four times daily.

In the above Example, the ethyl para-chlorophenoxyisobutyrate may be replaced by an equal weight of the sodium or potassium salts of 3,4-dimethylphenoxyisobutyric acid, 4-methoxyphenoxyisobutyric acid or 4-t-butylphenoxyisobutyric acid.

EXAMPLE 7

Capsules.

| | |
|---|---|
| Calcium carbonate powder | 2 g |
| Clofibrate | 2 g |

These ingredients were thoroughly mixed and formed into 1 gram capsules which were administered 3 or 4 times daily.

EXAMPLE 8

Capsules.

| | |
|---|---|
| Aluminium hydroxide | 4 g |
| Clofibrate | 2 g |

These ingredients were thoroughly mixed and formed into 0.75 g capsules two of which are administered four times daily.

EXAMPLE 9

Capsules.

| | | |
|---|---|---|
| Magnesium carbonate | 6 | g |
| Clofibrate | 1.5 | g |

These ingredients were thoroughly mixed and formed into eight capsules, two of which were administered four times daily.

EXAMPLE 10

Mixture of a powder and liquid.

| | |
|---|---|
| Calcium carbonate powder | 40 g |
| Calcium salt of para-chlorophenoxyisobutyric acid | 100 g |
| Talc (U.S.P.) | 10 g |
| Magnesium stearate (U.S.P.) | 0.5 g |

The finely powdered ingredients were thoroughly mixed and then filled into hard gelatin capsules for oral use, each capsule containing 500 mg. The capsules were taken thrice daily with meals.

In the above example, the para-chlorophenoxyisobutyric salt may be replaced by an equivalent amount of phenoxyisobutyric acid, 2-methyl-, 3-methyl-, or 4-methyl-phenoxyisobutyric acid, 3-chlorophenoxyisobutyric acid, 4-bromophenoxyisobutyric acid or 3-methyl-4-chlorophenoxy-isobutyric acid or a salt thereof.

EXAMPLE 11

Mixture of a powder and micro-encapsulated liquid.

| | | |
|---|---|---|
| Magnesium carbonate powder | 100 | g |
| ethyl para-chlorophenoxyisobutyrate (micro-encapsulated) | 150 | g |
| flavouring | 5 | g |
| gum arabic powder | 25 | g |

Because the ethyl ester has an unpleasant taste, it is conveniently mixed with the other components in the form of micro-capsules. The ethyl ester is micro-encapsulated to give a pore size of about 150 microns and then mixed with the other ingredients.

In this Example the ethyl para-chlorophenoxyisobutyrate may be replaced by an equal weight of n-propyl para-chlorophenoxyisobutyrate.

EXAMPLE 12

Mixture of powders.

| | |
|---|---|
| Magnesium salt of para-chlorophenoxy-isobutyric acid | 100 g |
| calcium chloride | 45 g |
| methyl cellulose | 10 g |
| Talc | 10 g |
| calcium stearate | 10 g |

The magnesium salt, calcium chloride are mixed well, granulated into three tablets (500 mg) for oral use and the tablets are taken thrice daily with meals.

In the above Example, the magnesium salt of para-chlorophenoxyisobutyric acid may be replaced by an equivalent amount of its potassium, calcium or aluminium salt.

EXAMPLE 13

Oil suspension.

| | | |
|---|---|---|
| polyunsaturated phosphatidyl choline (from soya beans) | 250 | g |
| ethyl para-chlorophenoxyisobutyrate | 250 | g |
| magnesium hydroxide | 250 | g |
| α-tocopherol acetate | 2.5 | g |
| mono- and di-glycerides | 120 | g |
| soya bean oil | 140 | g |

The above ingredients are mixed together for oral use. The oil base consists of equal parts of soya bean oil and purified linseed oil gelled with 1% by weight of aliminium monostearate. One teaspoonful is administered three times a day with meals.

EXAMPLE 14

Mixture with a third component which potentiates activity.

| parachlorophenoxyisobutyric acid | 100 g |
|---|---|
| magnesium carbonate | 100 g |
| oil base | 1000 ml |

The soya bean oil is mixed with the glyceride mixture and then poly-unsaturated phosphatidyl choline is dissolved with stirring and if necessary with heating in a water bath at 40°–50° C while protected by an inert gas, preferably also with exclusion of light. The α-tocopherol and ethyl ester were then added and the magnesium hydroxide worked in to give an oil suspension. The whole is then filled into hard gelatin capsules each containing 500 mg. Three capsules are given thrice daily with meals.

In the above Example, the ethyl para-chlorophenoxyisobutyrate may be replaced by an equal weight of 4-methoxyphenoxyisobutyric acid, 2:4-dichlorophenoxyisobutyric acid of 2:4:5-trichlorophenoxyisobutyric acid.

EXAMPLE 15

An emulsion.

| cane sugar | 200 | g |
|---|---|---|
| sodium benzoate | 1 | g |
| pyridoxine HCl | 0.6 | g |
| aluminium hydroxide | 750 | g |
| polyethylene sorbitanmono-oleate condensate | 10 | g |
| ethyl p-chlorophenoxyisobutyrate | 500 | g |
| soya bean lecithin | 25 | g |
| mixed tocopherol | 2.4 | g |
| propyl gallate concentrate | 0.05 | g |
| water | 400 | ml |

The cane sugar, sodium benzoate, pyridoxine and condensate are dissolved in the water and stirred into a mixture of the ester, lecithin, tocopherols and gallate. The aluminium hydroxide is then added and the resulting emulsion suspension is homogenised by passing through a conventional homogeniser. There is thus obtained an emuslion for oral administration for therapeutic purposes. About two teaspoonfuls (10 ml) are given three or four times daily.

In the above Example, the ethyl para-chlorophenoxyisobutyrate may be replaced by an equal weight of the sodium or potassium salts of 3,4-dimethylphenoxyisobutyric acid, 4-methoxyphenoxyisobutyric acid or 4-t-butylphenoxyisobutyric acid.

EXAMPLE 16

Capsules.

| Calcium carbonate powder | 0.9 g |
|---|---|
| calcium salt of para-chlorophenoxyisobutyric acid | 2 g |

These ingredients were thoroughly mixed and formed into 1 gram capsules which were administered 3 or 4 times daily.

EXAMPLE 17

Mixture of anion exchange resin, clofibrate derivative and metallic salt as a powder.

| Calcium carbonate | 40 g |
|---|---|
| Calcium salt of para-chlorophenoxyisobutyric acid | 100 g |
| PDX chloride | 1000 g |
| Gum arabic | 300 g |

The finely powdered ingredients are mixed thoroughly. For oral use, the powder is well mixed with water, a suitable daily dose being 20 g of the powder in three divided doses with meals.

In the above example the calcium salt of para-chlorophenoxyisobutyric acid can be substituted by the corresponding magnesium, aluminium or bismuth salt. Calcium carbonate can be replaced by magnesium carbonate, aluminium hydroxide or bismuth oxide. PDX chloride can be replaced by colestipol or cholest yramine.

EXAMPLE 18

Mixture of anion exchange resin, clofibrate derivative and metallic salt in tablets or capsules.

| Calcium carbonate | 20 g |
|---|---|
| Magnesium hydroxide | 80 g |
| Aluminium salt of para-chlorophenoxyisobutyric acid | 100 g |
| PDX chloride | 200 g |

The above ingredients are well mixed and filled into soft gelatin capsules.

Alternatively, to form tablets, the following additional ingredients are added:

| Talc | 10 g |
|---|---|
| Calcium stearate | 10 g | and the mixture formed into tablets. Three tablets (500 mg) are swallowed four times daily with meals.

In the above example calcium carbonate can be substituted by aluminium hydroxide, magnesium hydroxide by calcium chloride or bismuth carbonate. The aluminium salt of para-chlorophenoxyisobutyric acid can be substituted by the free acid or by its ethyl ester, potassium or sodium salt. PDX chloride can be replaced by colestipol or cholestyramine.

What I claim is:

1. A pharmaceutical composition for use in the treatment per os of hypercholesterolemia, which comprises a hypocholesteremic effective amount of
    a. a compound selected from p-chlorophenoxyisobutyric acid, the methyl, ethyl, propyl or butyl ester thereof or a sodium, potassium, calcium, magnesium, aluminum, zinc, bismuth or iron salt thereof, and
    b. an ingestible non-toxic bismuth salt capable of dissolution in human gastrointestinal juices, the total amount of non-toxic metal being from 3.2 to 90 equivalents per mole of p-chlorophenoxyisobutyric acid or ester or salt thereof.

2. A composition according to claim 1 wherein the total amount of non-toxic metal is from 4 to 15 equivalents per mole of p-chlorophenoxyisobutyric acid or ester or salt thereof.

3. A composition according to claim 1 wherein there is also present one or more ingestible non-toxic basic anion exchange resins, there being from 50 to 8000 grams of resin per mole of p-chlorophenoxyisobutyric acid or ester or salt thereof.

4. A composition according to claim 3 wherein the anion exchange resin is selected from cholestyramine, colestipol or poly-[2-(diethylamino)ethyl]-polyglycerylene dextran hydrochloride.

5. A composition according to claim 1 comprising ethyl p-chlorophenoxyisobutyrate and bismuth hydroxide.

6. A method for the treatment of hypercholesterolemia, in which there is administered to the patient per os a hypocholesteremic effective dose of a pharmaceutical composition comprising
   a. a compound selected from p-chlorophenoxyisobutyric acid, the methyl, ethyl, propyl or butyl ester thereof or a sodium, potassium, calcium, magnesium, aluminum, zinc, bismuth or iron salt thereof, and
   b. an ingestible non-toxic bismuth salt capable of dissolution in human gastrointestinal juices, the total amount of non-toxic metal being from 3.2 to 90 equivalents per mole of p-chlorophenoxyisobutyric acid or ester or salt thereof.

7. A method according to claim 6 wherein the composition contains a total amount of non-toxic metal from 4 to 15 equivalents per mole of p-chlorophenoxyisobutyric acid or ester or salt thereof.

8. A method according to claim 6 wherein the composition also contains one or more ingestible non-toxic basic anion exchange resins, there being from 50 to 8000 grams of resin per mole of p-chlorophenoxyisobutyric acid or ester or salt thereof.

9. A method according to claim 8 wherein the anion exchange resin is selected from cholestyramine, colestipol or poly-[2-(diethylamino)ethyl]-polyglycerylene dextran hydrochloride.

10. A method according to claim 6 wherein the composition comprises ethyl p-chlorophenoxyisobutyrate and bismuth hydroxide, said composition being administered in an amount sufficient to provide a daily dosage of about 1.5 g. of ethyl p-chlorophenoxyisobutyrate and about 2.0 g. of bismuth hydroxide.

* * * * *